United States Patent
Ratcliffe et al.

(10) Patent No.: US 9,820,847 B2
(45) Date of Patent: Nov. 21, 2017

(54) SYNTHETIC STRUCTURE FOR SOFT TISSUE REPAIR

(75) Inventors: Anthony Ratcliffe, Del Mar, CA (US); Andreas Kern, San Diego, CA (US)

(73) Assignee: Synthasome Inc., San Diego, CA (US)

(*) Notice: Subject to any disclaimer, the term of this patent is extended or adjusted under 35 U.S.C. 154(b) by 790 days.

(21) Appl. No.: 11/893,802

(22) Filed: Aug. 17, 2007

(65) Prior Publication Data

US 2008/0051888 A1 Feb. 28, 2008

Related U.S. Application Data (63) Continuation of application No. PCT/US2006/005946, filed on Feb. 21, 2006.

(60) Provisional application No. 60/654,569, filed on Feb. 18, 2005.

(51) Int. Cl.
*A61F 2/08* (2006.01)
*A61L 27/18* (2006.01)
*A61L 27/36* (2006.01)
*A61L 27/56* (2006.01)
*A61L 27/58* (2006.01)

(52) U.S. Cl.
CPC ............. *A61F 2/08* (2013.01); *A61L 27/18* (2013.01); *A61L 27/36* (2013.01); *A61L 27/56* (2013.01); *A61L 27/58* (2013.01)

(58) Field of Classification Search
CPC .................................... A61F 2/08; A61F 2/02
USPC ............. 623/13.11–13.2, 13.18, 23.72–23.75
See application file for complete search history.

(56) References Cited

U.S. PATENT DOCUMENTS

| | | | |
|---|---|---|---|
| 4,942,875 A * | 7/1990 | Hlavacek et al. | 606/230 |
| 4,987,665 A | 1/1991 | Dumican et al. | |
| 5,024,669 A | 6/1991 | Peterson et al. | |
| 5,061,283 A * | 10/1991 | Silvestrini | 128/898 |
| 5,263,984 A * | 11/1993 | Li et al. | 623/13.18 |
| 5,399,665 A | 3/1995 | Barrera et al. | |
| 5,492,697 A | 2/1996 | Boyan et al. | |
| 5,567,435 A | 10/1996 | Hubbell et al. | |
| 5,709,854 A | 1/1998 | Griffith-Cima et al. | |
| 5,900,245 A | 5/1999 | Sawhney et al. | |
| 5,906,934 A | 5/1999 | Grande et al. | |
| 6,123,727 A | 9/2000 | Vacanti et al. | |
| 6,129,761 A | 10/2000 | Hubbell | |
| 6,224,893 B1 | 5/2001 | Langer et al. | |
| 6,258,870 B1 | 7/2001 | Hubbell et al. | |
| 6,458,889 B1 | 10/2002 | Trollsas et al. | |

(Continued)

FOREIGN PATENT DOCUMENTS

| | | |
|---|---|---|
| JP | 2000-083979 A | 3/2000 |
| JP | 2003-512896 T | 4/2003 |

(Continued)

OTHER PUBLICATIONS

John McMurry, How Organic Reactions Occur: Mechanisms, Chapter 5, an Overview of Organic Reactions, Organic Chemistry, Third Edition, pp. 142-149.

(Continued)

*Primary Examiner* — Yashita Sharma
(74) *Attorney, Agent, or Firm* — Carter, DeLuca, Farrell & Schmidt, LLP (57) ABSTRACT

Synthetic structures for fibrous soft tissue repair include a polymeric fibrillar structure that exhibits mechanical properties of the human fibrous soft tissue.

21 Claims, 7 Drawing Sheets

Theoretical strain-stress curve for a biological tissue.

(56) References Cited

U.S. PATENT DOCUMENTS

| | | | |
|---|---|---|---|
| 6,465,001 B1 | 10/2002 | Hubbell et al. | |
| 6,471,993 B1 | 10/2002 | Shastri et al. | |
| 6,497,726 B1 | 12/2002 | Carter et al. | |
| 6,497,729 B1 | 12/2002 | Moussy et al. | |
| 6,554,867 B1 | 4/2003 | Joos | |
| 6,592,623 B1 * | 7/2003 | Bowlin et al. | 623/14.13 |
| 6,624,245 B2 | 9/2003 | Wallace et al. | |
| 6,924,370 B2 | 8/2005 | Chudzik et al. | |
| 2002/0095218 A1 * | 7/2002 | Carr, Jr. | A61F 2/0063 623/23.72 |
| 2004/0175408 A1 * | 9/2004 | Chun et al. | 424/426 |
| 2004/0267362 A1 | 12/2004 | Hwang et al. | |
| 2005/0196377 A1 | 9/2005 | Ratcliffe et al. | |
| 2006/0252981 A1 * | 11/2006 | Matsuda et al. | 600/37 |

FOREIGN PATENT DOCUMENTS

| | | |
|---|---|---|
| JP | 2004-321484 A | 11/2004 |
| JP | 2005278910 A | 10/2005 |
| JP | 2006094932 A | 4/2006 |
| WO | WO 93/17669 | 9/1993 |
| WO | WO 94/25080 | 11/1994 |
| WO | 03/043486 A2 | 5/2003 |
| WO | 03/057269 A2 | 7/2003 |
| WO | 03/092604 A2 | 11/2003 |
| WO | 2004/093932 A1 | 11/2004 |
| WO | 2004/101002 A2 | 11/2004 |
| WO | 2005/070340 A1 | 8/2005 |

OTHER PUBLICATIONS

Ton T. Hai et al., Surface Modification of Diaspirin Cross-linked Hemoglobin (DCLHb) with Chrondroitin-4-sulfate Derivatives, Part 1, Bioconjugate Chem. 2000, 11, pp. 705-713.

Roberto S. Benson, "Use of Radiation in Biomaterials Science", Nuclear Instruments and Methods in Physics Research B 191 (2002) pp. 752-757.

Japanese Office Action for Patent Application No. 2007-556385 dated Dec. 6, 2011.

\* cited by examiner

Figure 1. Theoretical strain-stress curve for a biological tissue.

Figure 2. Strain-stress curves for SIS®, GRAFTJACKET®, canine IFS tendon, and a woven mesh in accordance with the present disclosure.

Figure 3. Orientation of PLA meshes during stress-strain measurements.

Figure 4. Strain-stress curves for the tested materials.

Figures 5. Strain-stress curves for a mesh with 36 warp fibers per inch, and different densities of fill fibers.

Figures 6. Strain-stress curves for 52 Fill and different warp fibers.

Figure 7

SYNTHETIC STRUCTURE FOR SOFT TISSUE REPAIR

CROSS-REFERENCE TO RELATED APPLICATIONS

This application is a continuation of International Application No. PCT US/2006/005946 filed on Feb. 21, 2006 which claims benefit under 35 U.S.C. 119(e) of U.S. Provisional Application No. 60/654,569, filed Feb. 18, 2005, the entire disclosures of which are hereby incorporated by reference.

BACKGROUND

1. Technical Field

Synthetic structures for the repair of soft tissue are described. More specifically, fibrous structures that approximate the physical characteristics of soft tissue are useful as implants to promote the repair of soft tissue.

2. Background

There are currently several ways in which various types of soft tissues such as ligaments or tendons, for example, are reinforced and/or reconstructed. Suturing the torn or ruptured ends of the tissue is one method of attempting to restore function to the injured tissue. Sutures may also be reinforced through the use of synthetic non-bioabsorbable or bioabsorbable materials. Autografting, where tissue is taken from another site on the patient's body, is another means of soft tissue reconstruction. Yet another means of repair or reconstruction can be achieved through allografting, where tissue from a donor of the same species is used. Still another means of repair or reconstruction of soft tissue is through xenografting in which tissue from a donor of a different species is used. In addition, bioprosthetic devices for soft tissue attachment, reinforcement, and/or reconstruction have included a small intestinal submucosa (SIS) or other naturally occurring extracellular matrix (ECM), and a naturally occurring ECM or ECM component having a synthetic portion coupled thereto.

Using mesh in surgical procedures is well known. For example, surgical mesh may be used to support and/or reinforce a damaged or weakened portion of the body, for example in hernia repair. In this regard, often it is desirable for the mesh to be sufficiently porous to allow for growth of tissue through the graft after implantation. The healing tissue grows through porous openings in the implanted mesh, thereby assimilating the mesh and adding structural integrity to the tissue. Surgical mesh may be produced by knitting, weaving, braiding, or otherwise forming a plurality of yarns into a support trellis. Moreover, such mesh may be produced with monofilament or multifilament yarns made of materials such as polypropylene and polyester. Surgical mesh formed of monofilament yarn provides satisfactory reinforcement ability, but is often stiff and has limited pliability. In contrast, surgical mesh formed of multifilament yarn is often soft and pliable in comparison to mesh formed of monofilament yarn.

SUMMARY

A synthetic structure for human soft tissue repair includes a fibrillar structure that exhibits tensile properties of the human fibrous soft tissue. In certain embodiments, the fibrillar structure exhibits mechanical properties of human tendon and/or ligament. In some embodiments, the fibrous structure exhibits mechanical properties of a human ligament. In particularly useful embodiments, the fibrillar structure exhibits a stiffness in the range of about 20 to about 80 Newtons per millimeter (N/mm), and will exhibit a failure strain of 105% to 150%. The fibrillar structure can be woven, can have about 5 to about 80 warp fibers per inch, and may consist of 1 or more layers. The fibrillar structure can include one or more fibers having a diameter ranging from about 10 microns to about 200 microns. The fibrillar structure can be bioabsorbable or non-bioabsorbable.

In other embodiments, methods of repairing or reconstructing fibrous soft tissue is contemplated wherein a fibrillar structure that exhibits mechanical properties of the human fibrous soft tissue is affixed to tissue, such as muscle, bone, ligament or tendon in a manner that assists in the repair or reconstruction of fibrous soft tissue.

DETAILED DESCRIPTION OF PREFERRED EMBODIMENTS

A synthetic structure for human fibrous soft tissue repair includes a polymeric fibrous structure that exhibits mechanical properties of the human fibrous soft tissue. In certain embodiments, the fibrillar structure exhibits mechanical properties of human tendon and/or ligament. In some embodiments, the polymeric fibrillar structure exhibits mechanical properties of a human ligament. The mechanical properties of soft tissue and/or the polymeric fibrous structures in accordance with the present disclosure can be determined by any technique within the purview of those skilled in the art. For example, mechanical properties of soft tissue and/or the fibrous structures can be determined by the placing a sample in a spring loaded clamp attached to the mechanical testing device and subjecting the sample to constant rate extension (5 mm/min) while measuring load and displacement and recording the resulting strain-stress curve. In particularly useful embodiments, the polymeric fibrillar structure exhibits a stiffness in the range of stiffness exhibited by fibrous soft tissue. Typically, suitable stiffness will be in the range of about 10 to about 500 Newtons per millimeter (N/mm), and suitable tensile strength will be in the range of about 20 to about 2000 Newtons. In some embodiments, the stiffness of the polymeric fibrous structure will be in the range of about 20 to about 80 N/mm. In some embodiments, the fibrillar structure exhibits a failure strain at 105% to about 150% of original length.

The fibrous structure can be prepared using any method within the purview of those skilled in the art. For example, the fibrous structure can be woven. It is also contemplated that the fibrous structure could be a non-woven structure, provided that suitable mechanical properties are provided. In certain embodiments, the fibrous structure is woven and includes about 10 to about 150 warp fibers per inch. In some embodiments, the woven fibrous structure includes about 30 to about 100 warp fibers per inch. In particularly useful embodiments, the knitted or woven fibrous structure includes about 50 to about 75 warp fibers per inch.

The fibrillar structure can advantageously be prepared from fibers having a diameter ranging from about 10 microns to about 1.0 mm. In some embodiments, the fibrillar structure is prepared from fibers having a diameter ranging from about 10 microns to about 200 microns. In particularly useful embodiments, the fibrous structure is prepared from fibers having a diameter ranging from about 20 microns to about 50 microns. The fibrillar structure may be prepared from monofilaments, traditional multifilament yarns or bi-component multifilament yarns. It is further contemplated that the fibrillar structure can be prepared from fibers of at least two different diameters.

The dimensions of the fibrillar structure are not critical. In some embodiments in accordance with the present disclosure, a thin mesh is formed having a thickness in the range of about 0.05 millimeters to about 1.0 millimeters. The width and length dimensions of the fibrous structure can vary within those ranges conventionally used for a specific application and delivery device. For example, such ranges include dimensions of about 1 centimeter by 1 centimeter to about 15 centimeters by 15 centimeters. The present fibrillar structures can advantageously be dimensioned to allow them to be rolled or otherwise folded so as to fit within a cannula having a small diameter to allow arthroscopic or laparoscopic implantation. In particularly useful embodiments, the fibrillar structures in accordance with this disclosure define openings on the order of about 0.5 mm to about 2 mm. In some embodiments, the fibrous structure defines openings on the order of about 0.7 mm to about 1.3 mm.

The polymeric fibrillar structure can be made from any biocompatible polymeric material capable of providing suitable mechanical properties. The biocompatible material can be bioabsorbable or non-bioabsorbable. Suitable absorbable materials include glycolide, lactide, trimethylene carbonate, dioxanone, caprolactone, alklene oxides, ortho esters, polymers and copolymers thereof, collagen, hyaluronic acids, alginates, and combinations thereof. Suitable non-absorbable materials include, polypropylene, polyethylene, polyamide, polyalkylene therephalate (such as polyethylene therephalate polybutylene therephalate), polyvinylidene fluoride, polytetrafluoroethylene and blends and copolymers thereof.

It is further contemplated that a bioactive material can be applied to the fibrous structure. Suitable bioactive materials include, for example, extracellular matrix molecules such as fibronectin and laminin, growth factors such as EGF, FGF, PDGF and VEGF, hyaluronic acid, collagens, glycosaminoglycans, morphogens and chemoattractants. The bioactive materials can be applied to the fibrillar structure using any technique within the purview of those skilled in the art. For example, a solution of the bioactive agent in a suitable solvent can be prepared and the solvent driven off to leave the bioactive material deposited on the fibrillar structure. A further example is a bioactive agent that can be crosslinked around the fibrillar structure so as to embed the fibrillar structure within the bioactive agent.

Figure 7:
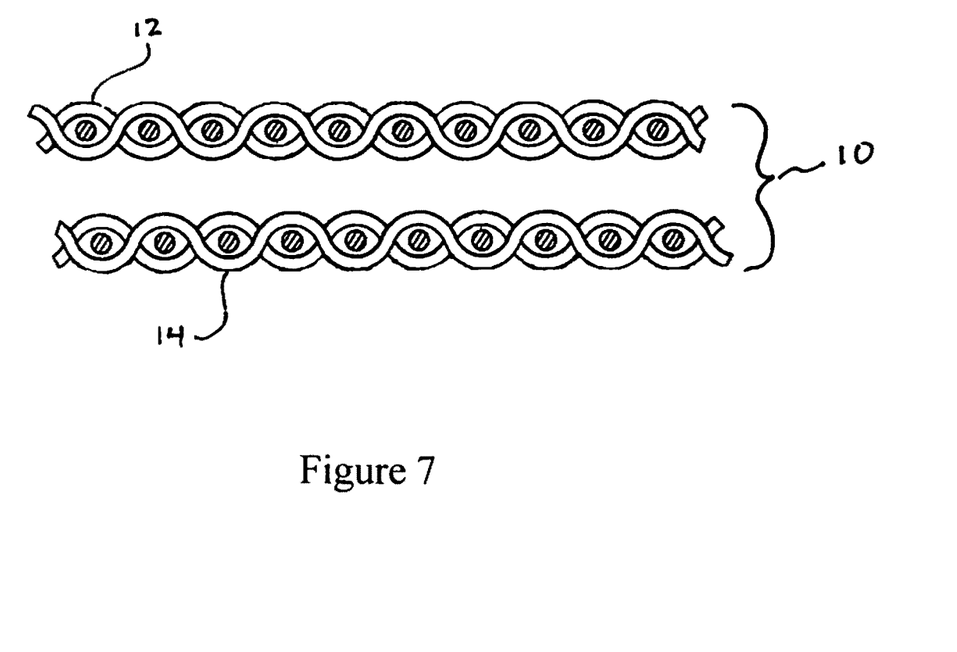
FIG. 7 schematically shows a repair device in accordance with an embodiment of the present disclosure that includes more than one layer of fibrillar structure.

It is further contemplated that more than one layer of fibrillar structure in accordance with the present disclosure can be combined to prepare a soft tissue repair device in accordance with other embodiments. See FIG. 7 wherein repair device 10 includes a first planar woven fibrillar structure 12 and a second planar woven fibrillar structure 14. Each of the two or more layers may have the same or different mechanical properties, provided that the combination of the two or more layers exhibits mechanical properties of soft tissue. In addition, each of the two or more layers may have the same or different bioabsorbability properties. In addition, each of the two or more layers may optionally have the same or different bioactive materials applied thereto.

The fibrillar structure can be packaged and sterilized in accordance with any of the techniques within the purview of those skilled in the art. The package in which the implant or plurality of implants are maintained in sterile condition until use can take a variety of forms known to the art. The packaging material itself can be bacteria and fluid or vapor impermeable, such as film, sheet, or tube, polyethylene, polypropylene, poly(vinylchloride), and poly(ethylene terephthalate), with seams, joints, and seals made by conventional techniques, such as, for example, heat sealing and adhesive bonding. Examples of heat sealing include sealing through use of heated rollers, sealing through use of heated bars, radio frequency sealing, and ultrasonic sealing. Peelable seals based on pressure sensitive adhesives may also be used.

The fibrillar structures described herein can be used to repair, support, and/or reconstruct fibrous soft issue. The fibrillar structures may rapidly restore mechanical functionality to the fibrous soft tissue. The fibrillar structures may be implanted using conventional surgical or laparoscopic/arthroscopic techniques. The fibrillar structure can be affixed to the soft tissue or to bone adjacent to or associated with the soft tissue to be repaired. In particularly useful embodiments, the fibrillar structure is affixed to muscle, bone, ligament, tendon, or fragments thereof. Affixing the fibrillar structure can be achieved using techniques within the purview of those skilled in the art using, for example, sutures, staples and the like, with or without the use of appropriate anchors, pledgets, etc.

The present fibrillar structure can be used alone or in combination with other tissue repair products within the purview of those skilled in the art. Presently known tissue repair products that can be used in combination with the present fibrillar structures include, for example, RESTORE® a small intestine submucosa (SIS) biologic graft material that is commercially available from Depuy Orthopedics Inc., Warsaw Ind.; GRAFTJACKET®, an acellular dermal tissue matrix commercially available from Wright Medical Technology, Inc., Arlington, Tenn.; and ENCUFF® a cross-linked pericardium xenograft that has been subjected to an anticalcification process commercially available from Selhigh, Inc., Union N.J. Other tissue repair products suitable for use in connection with the present fibrillar structures will be apparent to those skilled in the art. The other tissue repair product can be separate from or attached to the fibrillar structure.

In order that those skilled in the art may be better able to practice the compositions and methods described herein, the following examples are given as an illustration of the preparation of the present compositions and methods. It should be noted that the invention is not limited to the specific details embodied in the examples.

Example 1

Constant Rate Extension Test of Polylacetic Acid Thin Woven Mesh

Figure 1:
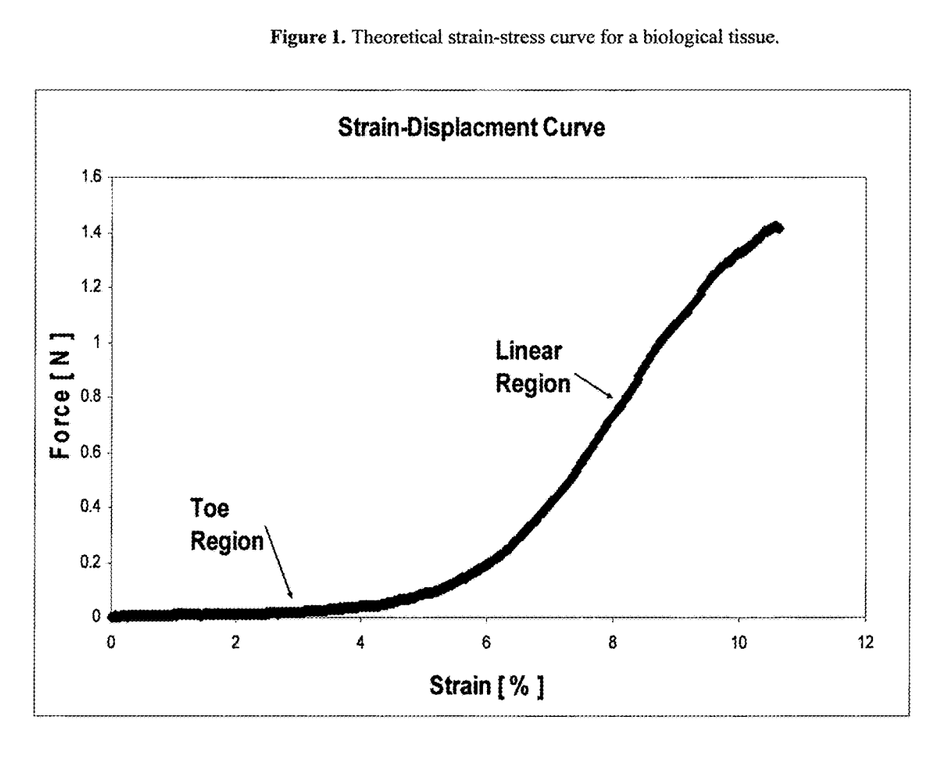
FIG. 1 shows Strain-stress curves for SIS®, GRAFTJACKET®, canine infraspinatus (IFS) tendon and a mesh in accordance with the present disclosure.

The purpose of this experiment was to determine the mechanical properties of a thin woven polylacetic acid (PLA) consisting of 52 Warp by 52 Fill fibers compared to RESTORES a small intestine submucosa (SIS) biologic graft material that is commercially available from Depuy Orthopedics Inc., Warsaw Ind., GRAFTJACKET® an acellular dermal tissue matrix commercially available from Wright Medical Technology, Inc., Arlington, Tenn. and canine infraspinatus (IFS) tendon. As illustrated in FIG. 1, as biological tissues are extended there may be two regions over which the mechanical properties may be drastically different; a toe region where the matrix components may be crimped or unorganized; and a linear region where the matrix components may align in the direction of extension leading to increased loads during extension.

Figure 2:
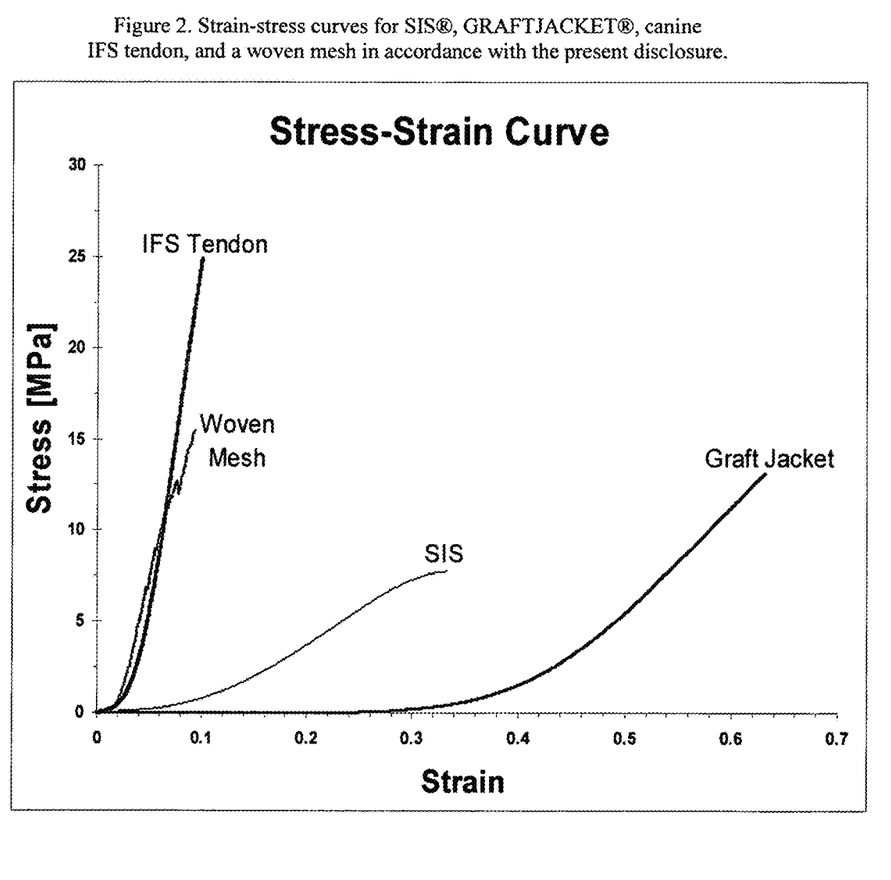
FIG. 2 shows a theoretical strain-stress curve for a biological tissue.

The samples were placed in a spring loaded clamp attached to the mechanical testing device and subjected to constant rate extension (5 mm/min), while measuring load and displacement. The strain-stress curve was recorded for each sample and the data were compared to that obtained for IFS tendon. As seen in FIG. 2, the tensile properties of the thin woven mesh is comparable to that of the IFS tendon

Example 2

Figure 3:
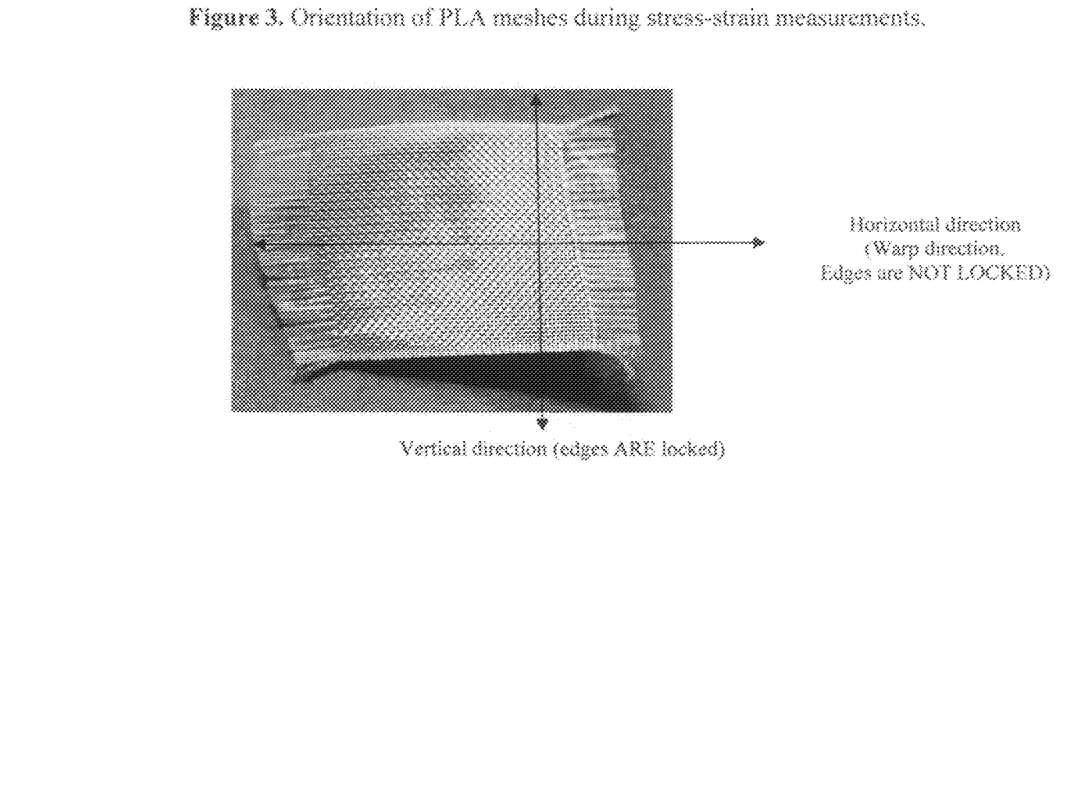
FIG. 3 shows the orientation of PLA woven meshes during stress-strain measurements.

Constant Rate Extension Test of Polylacetic Acid Woven Meshes of Varying Warp and Fiber Structures The purpose of this experiment was to determine the mechanical properties of a series of woven polylacetic acid (PLA) meshes constructed with a defined number of warp and fill fibers. Included in the study were samples of human and canine infraspinatus (IFS) tendon to provide a comparison of the strength of natural tendon. The data can be used to develop a relationship between the number of warp and fill fibers required to design meshes with mechanical properties approximating human or canine IFS tendon. The samples were tested in a mechanical testing device under identical conditions. All of the meshes were tested in their horizontal direction wherein the ends of the fibers were not locked (See FIG. 3).

The samples were placed in a spring loaded clamp attached to the mechanical testing device and subjected to constant rate extension (5 mm/min), while measuring load and displacement. The data were analyzed to determine ramp modulus (stiffness) and strain at a load of 2 Newtons (N). The ramp modulus was computed between 25 and 75% of the maximum load recorded. In addition, the strain-stress curve was recorded for each sample and the data were compared to that obtained for human and canine IFS tendon. Table 1 shows the numbers of warp and fill fibers for the samples tested in this study.

TABLE 1

Different mesh designs involved in the study.

| Scaffold's Number, Number of Samples | Number of Warp (W) Fibers | Number of Fill (F) Fibers |
|---|---|---|
| 1, n = 1 | 36 | 36 |
| 2, n = 1 | 36 | 52 |
| 3, n = 1 | 36 | 60 |
| 4, n = 1 | 52 | 36 |
| 5, n = 3 | 52 | 52 |
| 6, n = 1 | 52 | 60 |
| 7, n = 1 | 60 | 36 |
| 8, n = 1 | 60 | 52 |
| 9, n = 1 | 60 | 60 |

Figure 4:
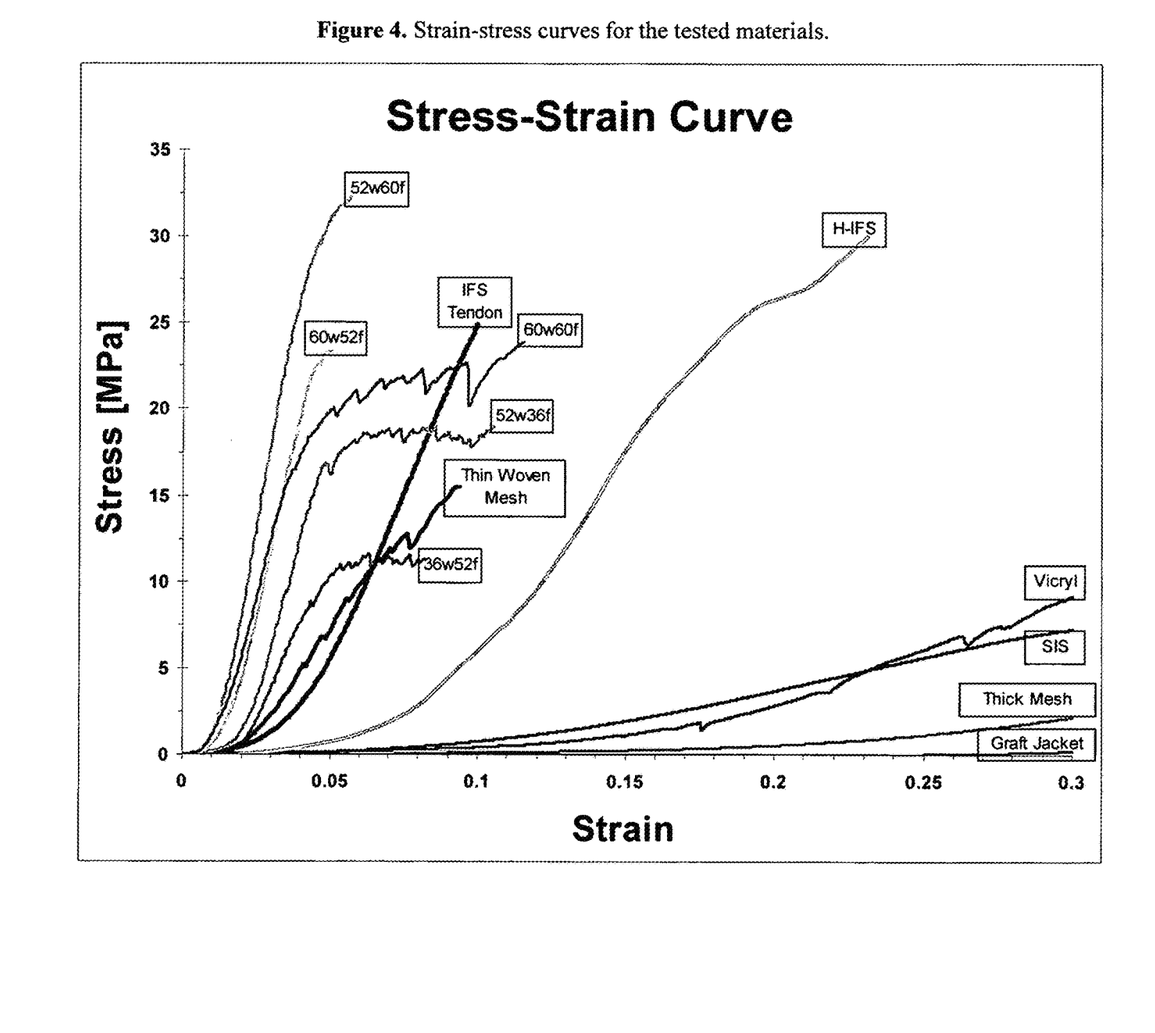
FIG. 4 shows strain-stress curves for a variety of materials tested, including SIS®, GRAFTJACKET®, a thick mesh, VICRYL®, IFS tendon and various meshes in accordance with the present disclosure.
Figure 5:
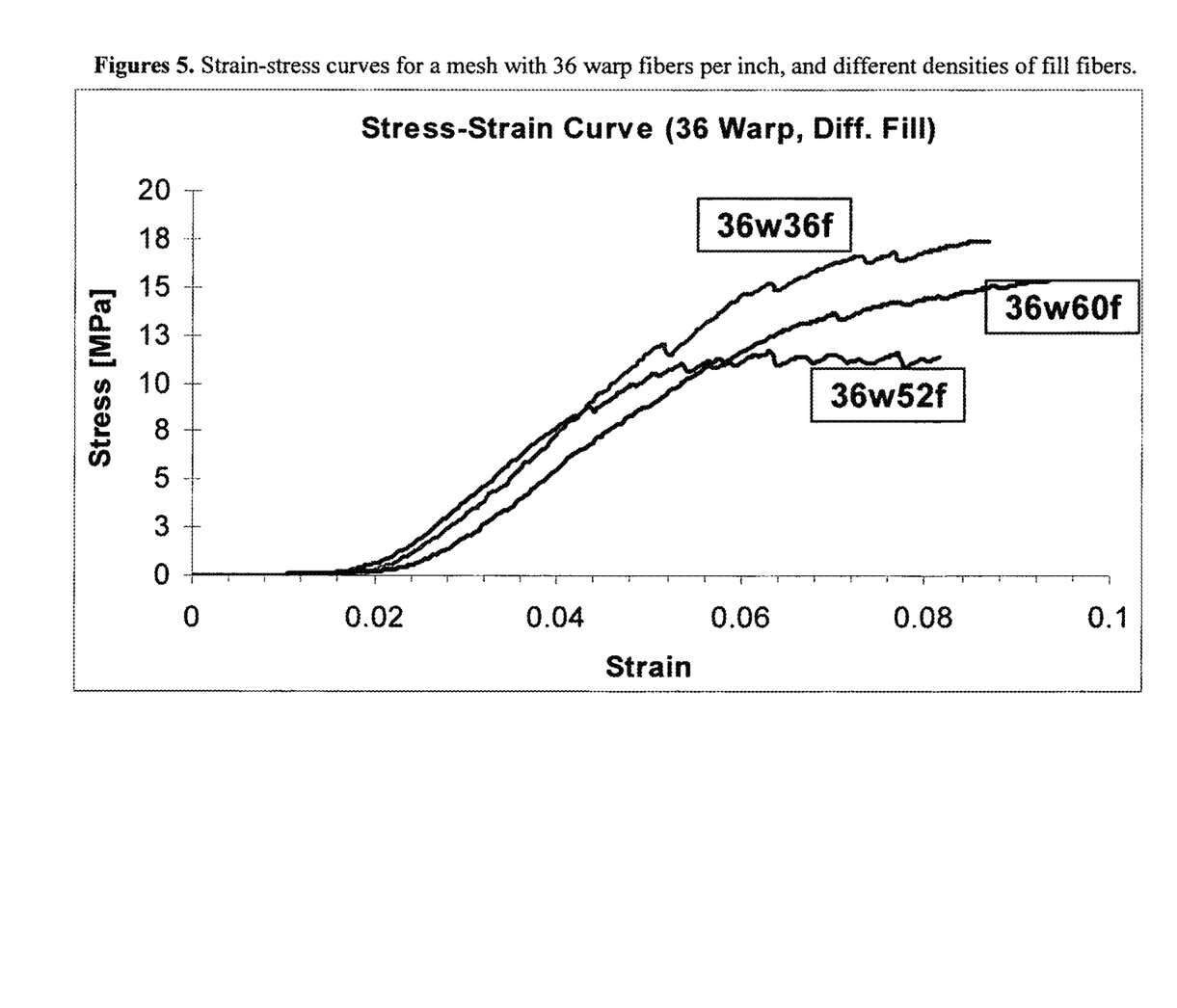
FIG. 5 shows strain-stress curves for meshes made with 36 warp and (A) 36 fill, (B) 52 fill, (C) 60 fill fibers demonstrating that the density of fill fibers does not have a significant impact on the tensile stiffness of the mesh.
Figure 6:
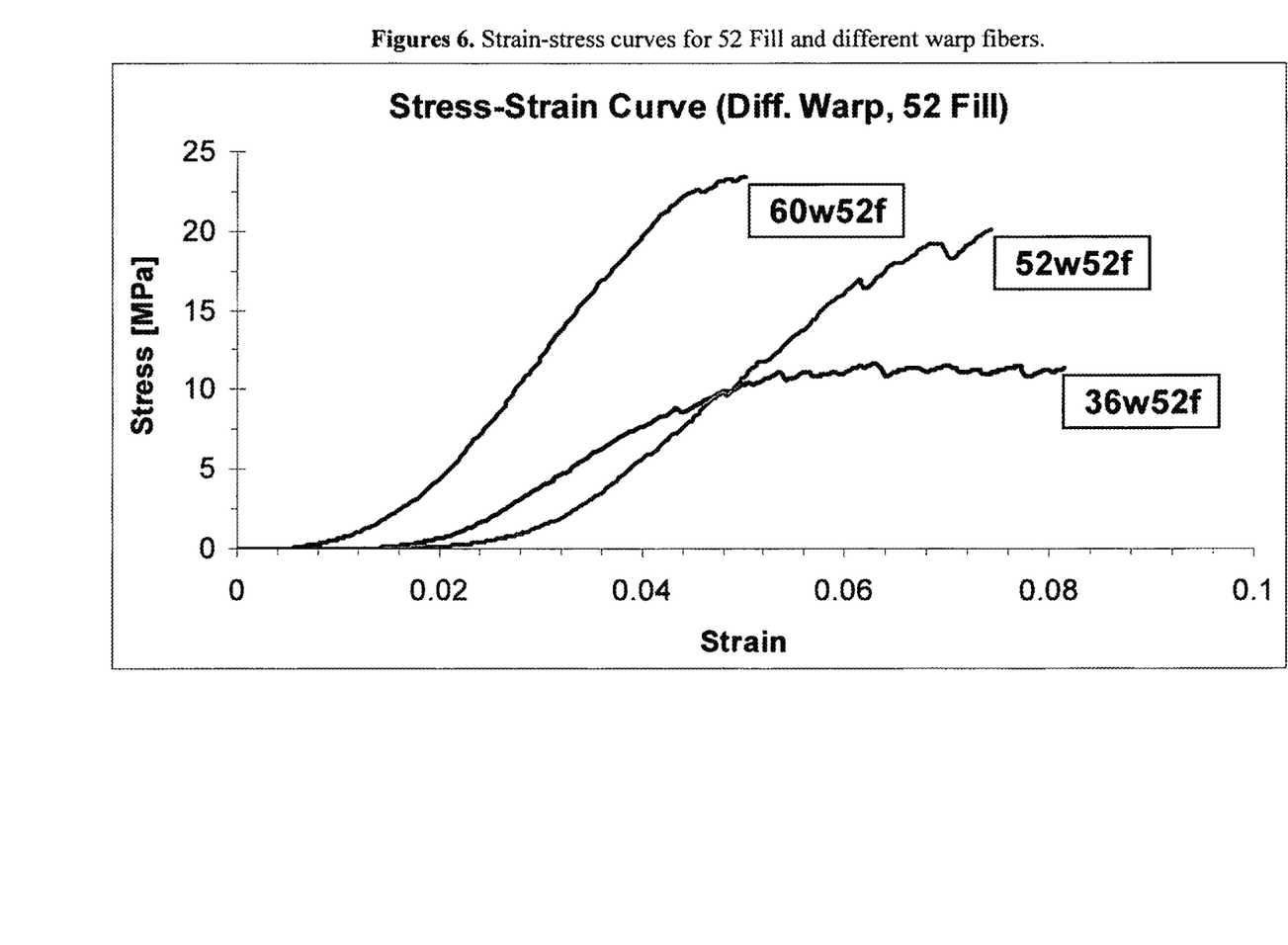
FIG. 6 shows strain-stress curves for meshes with a fill density of 52 fibers/inch with (A) 36 warp, (B) 52 warp, and (C) 60 warp fibers per inch, demonstrating increased tensile properties with increased warp fiber density.

The strain-stress curves for some of the materials tested are shown in FIG. 4. The results demonstrate that the mechanical properties of the meshes can be greater than, similar to, or less than human and canine IFS tendon, depending on the fabrication of the mesh. In FIG. 5 the stain-stress curves are grouped according to the number of warp fibers to examine a potential relationship between the mesh architecture and the resulting mechanical properties. The results show that the number of fibers in the fill direction do not significantly affect the tensile properties of the fibrillar structure. Since the constant rate extension test is done in the warp direction, the fibers in the fill direction should not contribute to the strength of the mesh. As can be seen in FIG. 6, the higher number of warp fibers resulted in a steeper slope in the linear region of the graph which is confirmed with the average ramp modulates of 356, 557, and 562 MPa for 36, 52 and 60 warp fibers respectively.

Since the constant rate extension test is done in the warp direction the increase in the number of warp fibers when there is the same number of fill fibers should result in an increase in the strength of the mesh in that direction Table 2 shows the maximum loads for each of the mesh dimensions tested. Those skilled in the art know that the maximum load tolerated by the rotator cuff tendon is in the range of 550-1,800 N. In addition, a synthetic tendon should have a strength with a minimum value of approximately 40% of the lower range or about 220 N, to perform in the functional mechanical range of a rotator cuff tendon. Therefore, according to the data in Table 2, a 2 inch wide repair device would require about 2-3 layers of mesh to satisfy the load requirement. As those skilled in the art will appreciate, the number of layers required depends on the selected warp and fill fiber numbers. In some cases, a slight increase in the width of only one layer, for example from 2 inches to 3.2 inches would satisfy the maximum load tolerated by the mesh.

TABLE 2

Maximum load tolerated with each mesh.

| #W × #F | Width [mm] | Max load [g] | Max load [N] | Max Load 1 layer, 2" wide [N] | Max Load 2 layers, 2" wide [N] | Max Load 3 layers, 2" wide [N] |
|---|---|---|---|---|---|---|
| 36 × 36 | 10.16 | 1607.82 | 15.8 | 79 | 158 | 237 |
| 36 × 52 | 11.25 | 675.37 | 6.6 | 30 | 60 | 90 |

TABLE 2-continued

Maximum load tolerated with each mesh.

| #W × #F | Width [mm] | Max load [g] | Max load [N] | Max Load 1 layer, 2" wide [N] | Max Load 2 layers, 2" wide [N] | Max Load 3 layers, 2" wide [N] |
|---|---|---|---|---|---|---|
| 36 × 60 | 12.45 | 1294.92 | 12.7 | 52 | 104 | 155 |
| 52 × 36 | 9.56 | 1519.71 | 14.9 | 79 | 159 | 238 |
| 52 × 52 (1) | 10.25 | 1552.50 | 15.2 | 75 | 151 | 226 |
| 52 × 52 (2) | 10.18 | 959.24 | 9.4 | 47 | 94 | 141 |
| 52 × 52 (3) | 9.92 | 1177.77 | 11.6 | 59 | 118 | 178 |
| 52 × 60 | 10.00 | 2682.20 | 26.3 | 134 | 267 | 401 |
| 60 × 36 | 11.00 | 1061.37 | 10.4 | 48 | 96 | 144 |
| 60 × 52 | 10.80 | 2145.01 | 21.0 | 99 | 198 | 297 |
| 60 × 60 | 11.38 | 3125.52 | 30.7 | 137 | 274 | 411 |
| C-SSP Tendon | 12.14 | 895.15 | 8.8 | 4.12 | N/A | N/A |
| C-SubS Tendon | 12.21 | 622.30 | 6.1 | 1.41 | N/A | N/A |

The data shown above can be used to calculate the maximum tolerated load for each warp fiber as a function of the number of fill fibers (Table 3). As can be seen from the data in table 4, the maximum load per warp fiber is very similar for the meshes with different numbers of fill fibers. The average maximum load is 0.764 N and therefore to construct a mesh that would tolerate a maximum load of 220 N would require 228 Warp fibers.

TABLE 3

Maximum load for each Warp fiber.

| Description | Max Load for Warp × Ave. Fill [N/in] | Max Load/ # Warp [N/Warp Fiber] | Max Load/# Warp AVERAGE [N/Warp Fiber] |
|---|---|---|---|
| 36 W × Average Fill | 27 | 0.744 | 0.764 |
| 52 W × Average Fill | 39 | 0.759 | |
| 60 W × Average Fill | 47 | 0.789 | |

The conclusions from this study include that the meshes can be purposely designed to have specific mechanical properties, and these can be similar to the mechanical properties of human and canine IFS tendon. Therefore, the meshes would be of sufficient strength to repair a human rotator cuff tendon injury. Specifically, it was determined that the number of warp fibers influences the maximum tolerated load and that the load tolerated per warp fiber is approximately 0.764 N. These data provide the information required to select the width of a mesh to affect a desired tendon repair and determine the number of warp fibers required to provide the necessary maximum tolerated load.

It will be understood that various modifications may be made to the embodiments disclosed herein. Therefore, the above description should not be construed as limiting, but merely as exemplifications of preferred embodiments. Those skilled in art will envision other modifications within the scope and spirit of the claims appended hereto.

What is claimed is:

1. A synthetic structure for repair of a rotator cuff comprising a polymeric fibrillar structure having a length and a width and having uniform fibrillar distribution, a stiffness of about 10 to about 500 Newtons per millimeter (N/mm) along the length and along the width, and at least one fiber having a diameter ranging from about 10 microns to about 200 microns, wherein the fibrillar structure is a planar woven structure, the planar woven structure exhibiting mechanical properties of human rotator cuff tendon.

2. The synthetic structure of claim 1, wherein the polymeric fibrillar structure is bioabsorbable.

3. The synthetic structure of claim 2, wherein the polymeric fibrillar structure is fabricated from at least a member selected from the group consisting of glycolide, lactide, trimethylene carbonate, dioxanone, caprolactone, alkylene oxides, ortho esters, polymers and copolymers thereof, collagen, hyaluronic acids, alginates, and combinations thereof.

4. The synthetic structure of claim 1, wherein the polymeric fibrillar structure is non-bioabsorbable.

5. The synthetic structure of claim 4, wherein the polymeric fibrillar structure is fabricated from at least a member of the group consisting of polypropylene, polyethylene, polyamide, polyalkylene terephthalate, polyvinylidene fluoride, polytetrafluoroethylene and blends and copolymers thereof.

6. The synthetic structure of claim 1, wherein the polymeric fibrillar structure exhibits a tensile strength of about 20 to about 2000 Newtons.

7. The synthetic structure of claim 1, wherein the polymeric fibrillar structure exhibits a failure strain at 105% to about 150% of original length.

8. The synthetic structure of claim 1, wherein the polymeric fibrillar structure exhibits a tensile strength of at least about 220 Newtons.

9. The synthetic structure of claim 1, wherein the polymeric fibrillar structure has about 10 to about 150 warp fibers per inch.

10. The synthetic structure of claim 1, wherein the polymeric fibrillar structure has about 30 to about 100 warp fibers per inch.

11. The synthetic structure of claim 1, wherein the polymeric fibrillar structure has about 50 to about 75 warp fibers per inch.

12. The synthetic structure of claim 1, wherein the polymeric fibrillar structure is knitted.

13. The synthetic structure of claim 1, wherein the polymeric fibrillar structure is non-woven.

14. The synthetic structure of claim 1, wherein the polymeric fibrillar structure comprises at least one fiber having a diameter ranging from about 30 microns to about 100 microns.

15. The synthetic structure of claim 1, wherein the polymeric fibrillar structure comprises at least one fiber having a diameter ranging from about 50 microns to about 80 microns.

16. The synthetic structure of claim 1, wherein the polymeric fibrillar structure comprises at least two fibers of different diameters.

17. The synthetic structure of claim 1, wherein the polymeric fibrillar structure has at least two layers.

18. The synthetic structure of claim 1, wherein the polymeric fibrillar structure includes a bioactive agent thereon.

19. The synthetic structure of claim 18 wherein the bioactive agent is selected from the group consisting of extracellular matrix molecules, growth factors and hyaluronic acid.

20. A synthetic structure for repair of a rotator cuff comprising a polymeric fibrillar structure, wherein the fibrillar structure comprises two planar woven layers having the same mechanical properties, the fibrillar structure exhibiting a stiffness of about 10 to about 500 Newtons per millimeter (N/mm), a tensile strength of about 20 to about 2000 Newtons and a failure strain at 105% to about 150% of original length.

21. A synthetic structure comprising:
a rectangular, bioabsorbable polymeric fibrillar structure configured for human rotator cuff tendon repair and having two planar woven layers, each of the two planar woven layers having the same mechanical properties and a uniform fibrillar distribution.

* * * * *